United States Patent [19]

Mintzis et al.

[11] Patent Number: 5,422,366
[45] Date of Patent: Jun. 6, 1995

[54] TREATMENT OF FUNGAL INFECTIONS

[75] Inventors: Medwin M. Mintzis, New York, N.Y.; N. Ross Buckenham, Alameda, Calif.; Donald G. Rosellini, Kew Biscayne, Fla.

[73] Assignee: Advanced Oxygen Technologies, Inc., Alameda, Calif.

[21] Appl. No.: 166,663

[22] Filed: Dec. 13, 1993

Related U.S. Application Data

[63] Continuation of Ser. No. 809,449, Dec. 18, 1991, abandoned.

[51] Int. Cl.$^6$ .................. A01N 43/08; A01N 55/02; A61K 31/34; A61K 31/295
[52] U.S. Cl. .................................... 514/474; 514/502; 514/566
[58] Field of Search ............... 514/502, 566, 781, 474

[56] References Cited

U.S. PATENT DOCUMENTS

| | | |
|---|---|---|
| 3,395,236 | 7/1968 | White . |
| 4,810,498 | 3/1989 | DiMeglio . |
| 4,898,878 | 2/1990 | Shapiro et al. ............... 514/386 |

FOREIGN PATENT DOCUMENTS

| | | |
|---|---|---|
| 3720147 | 12/1988 | Germany . |
| 2202743 | 10/1988 | United Kingdom . |
| 8702580 | 5/1987 | WIPO . |
| 9102538 | 3/1991 | WIPO . |

OTHER PUBLICATIONS

Brochure, Treatment of Onchomycosis with Topical Fungi-Nail, Kreindler et al. (1961).

*Primary Examiner*—Howard T. Mars
*Assistant Examiner*—Rebecca Cook
*Attorney, Agent, or Firm*—Townsend and Townsend Khourie and Crew

[57] ABSTRACT

Fungal nail infections are treated by depriving aerobic fungi of oxygen by forming an oxygen barrier over the exposed surface of an infected nail. Conveniently, the oxygen barriers are formed by applying a liquid film-forming carrier comprising an oxygen-scavenging substance, such as transition metal chelate or complex of salicylic acid or a salicylate, an oxidizable organic acid or alcohol in combination with a catalyzing agent, or a polycarboxylic acid chelate or complex of a transition metal or transition metal salt.

10 Claims, No Drawings

TREATMENT OF FUNGAL INFECTIONS

This is a continuation of application Ser. No. 07/809,449 filed Dec. 18, 1991 now abandoned.

BACKGROUND OF THE INVENTION

1. Field of the Invention

The present invention relates generally to methods and compositions for treating fungal nail infections. More particularly, the present invention relates to the treatment of fungal nail infections by oxygen deprivation.

Many adults suffer from chronic fungal infections of the fingernails or toenails. Most such infections are causes by obligate aerobic fungal species, usually "dermatophytic" or yeast-like fungi, which infect the nail plate itself. Although not usually imposing a significant health risk, such nail infections frequently cause the nail to become deformed, discolored and/or blackened. Thus, there is a strong desire among infected individuals to treat the infection and return their nails to a normal appearance.

Unfortunately, such fungal nail infections have proven to be very resistant to treatment. Systemic administration of anti-fungal drugs is hindered by limited blood circulation in the nail bed and poor transport to the nail plate, requiring high dosage levels for long periods of time. Such high drug dosages can have adverse side effects, and it has been found that clearance of the infection is often only temporary. Thus, systemic treatment must often be continued indefinitely.

Topical administration of anti-fungal drugs also suffers certain limitations. The nail plate is a relatively thick structure which inhibits penetration of the drug being applied. Moreover, the topical application of creams, lotions, gels, and the like, is often lost or dissipated in relatively short times. Although attempts have been made to incorporate such topically active anti-fungal drugs into film-forming compositions, e.g., nail polishes or lacquers, to improve drug persistence, such approaches have not proved entirely satisfactory. While removal of the nail can improve topical drug treatment, the ability to maintain a constant supply of the drug to the nail bed remains problematic.

For these reasons, it would be desirable to provide improved methods and compositions for treating fungal nail infections. Such methods and compositions should be effective in treating the initial infection as well as inhibiting spread of the infection to other nails and recurrence of the infection after treatment has been completed. It would be desirable to provide treatment methods and compositions which do not rely on the administration of anti-fungal drugs, either systemically or topically. In particular, the treatment methods and compositions should avoid the side effects which can accompany drug administration. Additionally, it would be desirable to provide methods and compositions which can provide cosmetic cover-up during the treatment period.

2. Description of the Background Art

Treatment of nail fungal infections with anti-fungal drugs incorporated in a film-forming vehicle is described in PCT application WO 87/02580 and UK Patent Application 2 202 743A. Other compositions incorporating anti-fungal drugs for topical treatment of nail fungal infections are described in U.S. Pat. Nos. 4,810,498 and 3,395,236. Fungi-Nail ® is a commercial formulation for the topical treatment of fungal nail infections which includes 2% salicylic acid in combination with anti-fungal drugs. The formulation does not form an oxygen barrier when applied to the nail.

SUMMARY OF THE INVENTION

According to the present invention, chronic infections of the fingernail and toenail by aerobic fungi are treated by depriving the fungi of oxygen for a time sufficient to inhibit growth of the fungi, usually over a time period sufficient to permit full regrowth and replacement of the nail. In a specific embodiment, an oxygen barrier film is applied to the nail to inhibit oxygen penetration through the nail to fungi present in the nail bed. Conveniently, the oxygen barrier film may be applied as a liquid carrier which includes a suitable oxygen-scavenger substance.

The present invention further comprises compositions for treatment of nail fungal infections, where the compositions include an oxygen-scavenging substance present in a liquid film-forming carrier. The liquid film-forming carrier may conveniently be a varnish, polish, or lacquer comprising a resin dispersed or dissolved in a solvent. The oxygen-scavenger may be any of a variety of substances which can bind to, or react with, oxygen to prevent its penetration through the film formed after the carrier is applied to the nail. Exemplary oxygen-scavenging substances include transition metal chelates or complexes of salicylate acid or salicylate salts; oxidizable organic acids, alcohols, or derivatives thereof, in combination with a catalyzing agent; and polycarboxylic acid chelates or complexes of a transition metal or a transition metal salt.

Treatment methods and compositions according to the present invention based on oxygen deprivation of aerobic fungi have substantial advantages over previous treatments. Oxygen deprivation has been found to be clinically effective in inhibiting aerobic fungal growth, usually being able to eliminate infection by treatment of the nail through an entire replacement growth cycle. The treatments of the present invention are characterized by little or no recurrence of infection in untreated nails and minimum or no spreading of the infection from one nail to another. Moreover, the methods do not require use of an active anti-fungal drugs, thus there are no apparent side effects. Additionally, the compositions of the present invention can be formulated as a nail polish where coloring provided by the composition can improve the cosmetic appearance of the nail.

DESCRIPTION OF THE SPECIFIC EMBODIMENTS

The present invention provides methods and compositions for treating fingernails and toenails which have been infected by aerobic fungi. Such fungal infections occur in the nail plate, which is the hardened, translucent layer overlying the nail bed on the dorsal surface of each finger and toe. Surprisingly, it has been found that inhibiting oxygen penetration into the nail from its upper, exposed surface (and preferably the face edges) is sufficient to kill or prevent proliferation of the fungi within the nail. In particular, it has been found that there will be insufficient oxygen transport from circulation in the nail bed to support growth of fungi within the nail.

As fungal spores may remain viable, however, it will usually be necessary to continue oxygen deprivation treatment according to the present invention for a time sufficient to permit full regrowth of the nail. In this way, viable spores will be eliminated with the old nail plate as it is removed. Treatment according to the present invention will prevent infection of the new nail growth as well as preventing infection of other fingernails and toenails.

Fungal infections which may be treated according to the present invention include infections from yeasts, such as Candida species, most notably albicans; from dermatophytes, such as *Trichophyton mentagrophytes, Trichophyton rubrum, Trichophyton megninii, Trichophyton schoenleinii, Trichophyton tonsurans,* and Microsporum species; from molds, such as *Scopulariopsis cephalosporium,* and *Aspergillus fusarium;* from Epidermophyton species; and from *Hendersonula toruloideo.*

Fungal nail infections which may be treated using the methods and compositions of the present invention are usually characterized by tarnished white, yellowed, or blackened nails. The nails will usually pull away from the pink nail bed along the sides or outer edges, and infections are usually exacerbated by hot, damp conditions inside the shoes or in environments where hands or feet are continually exposed to moisture. The fungal infections are most commonly found in the toenails and can spread from toe to toe, foot to foot, and foot to hand. Diagnosis of the fungal infections may be microscopic identification and/or culture of the infected areas.

Specific infections which may be treated by the methods and compositions of the present invention include distal subungual onychomycosis (caused by infection with *Candida trichophyton,* Scopularosis, and Aspergillis); superficial white onychomycosis (caused by *Trichophyton mentagrophytes*); proximal white subungual onychomycosis (caused by Trichophyton species); total secondary dystrophic onychomycosis (caused by yeast and Trichophytons); and total dystrophic primary onychomycosis (caused by Candida species).

The methods of the present invention rely on depriving the fungal species responsible for the onychomycosis of oxygen for a time sufficient to inhibit growth of the fungi, usually for a time sufficient to permit full replacement growth of the treated nail so that all spores and other infective material will be eliminated. Oxygen deprivation will usually be accomplished by applying an oxygen-barrier film over the exposed surface of the infected nail to inhibit oxygen transport to the fungi on and within the nail plate. It has been found that the nail plate itself is sufficiently oxygen impermeable so that oxygen will not reach the fungi from the nail bed beneath the nail plate. In particular, the oxygen permeability should be sufficiently low to result in growth inhibition of substantially all fungi, present on the nail.

Suitable materials for the oxygen-barrier film will usually be organic polymer films having low oxygen permeabilities, such as polyvinyl alcohols, ethylene-vinyl alcohols, polyacrylonitriles, polyvinylidene chloride polymers and copolymers, polyesters (formulated to have low oxygen permeabilities, polymethacytylene-diamine, nylons and polyethyleneterephthalates (PET). The films may be preformed with a thickness sufficient to prevent oxygen penetration sufficient to permit growth of the fungi, as set forth above.

Conveniently, the oxygen barrier will be applied as a film-forming liquid over the exposed surface of the nail plate, where the resulting solidified film will have the requisite oxygen barrier properties. To decrease the oxygen permeability, two or more layers of the film-forming liquid may be applied, with successive layers being applied after the underlying layer has dried. Alternatively, it will be possible to apply the pre-formed films or other materials over the nail surface, frequently using adhesives, bandages, or the like, to maintain the materials in place. In particular, the films may include a pressure sensitive adhesive on one surface thereof.

In the case of pre-formed films, the film will usually be patterned or sized appropriately (into nail-sized segments) so that they may be placed directly on the infected nail without additional cutting. Alternatively, a sheet of the material may be provided, and the patient may cut to size prior to use. In either case, the film material will be stored in an oxygen-free enclosure so that its oxygen absorbing capacity will not be exhausted prior to use.

Preferred compositions for use in the method of the present invention will comprise an oxygen-scavenging substance present in the film-forming liquid in an amount sufficient to further reduce oxygen penetration in the resulting films, preferable to a very low level beyond that possible with polyene films without an incorporated scavenger. The incorporation of suitable oxygen-scavenging substances permits the use of liquid carriers which otherwise would not form adequate oxygen barrier films for use in the present invention. For example, addition of suitable oxygen-scavenging substances, as described below to conventional nail polish formulations will permit the use of such polishes for therapeutic treatment according to the present invention. The use of formulations which are similar to conventional nail polishes has a number of advantages. People are familiar with using nail polishes which will facilitate treatment and contribute to a high compliance rate. The nail polishes can contain pigments so that they can be used cosmetically in a generally conventional manner. Finally, the packaging of the compositions can be similar to that for conventional nail polishes, i.e., the liquid carriers can be placed in bottles having brush applicators.

The concentrations and distributions of oxygen-scavenging substances may be selected to reduce the oxygen permeability of a film to well below that obtained with conventional polymeric films without oxygen-scavenging substances (at least until the oxygen-scavenging substance has been exhausted within the film). Thus, it is believed that oxygen permeabilities well below 0.1 cc/mil/100 in$^2$/day/atm $O_2$ (the value for a very low oxygen permeability material) can be achieved.

Suitable film-forming carriers will be storable as liquids and be capable of dissolving or suspending the oxygen-scavenging substance(s), as described in more detail hereinafter. Usually, the film-forming liquid carriers will comprise one or more resin(s) present in an organic solvent, where the resin will form a thin film over the infected nail after it is applied, typically by brushing. Suitable film-forming resins include cellulose resins, particularly nitrocellulose and dinitrocellulose; ethylene oxide resins; acrylic acid and acrylate resins; vinyl resins; and polyvinyl pyrrolidone resins. Suitable organic solvents include low and medium boiling point alcohols, aromatic hydrocarbons, aliphatic hydrocarbons, and the like. The film-forming liquid carriers may further comprise plasticizers, such as high molecular weight esters including dibutyl phthalate, di(2-ethylhexyl) phthalate, triethyl citrate, and acetyl tributyl citrate, and the like. Pigments may also be provided when it is desired to provide color in the compositions for cosmetic purposes.

Particular formulations for the liquid film-forming carrier are described in PCT Patent Application No. WO 87/02580 and U.K. Patent Application No. GB 2 202 743 A. Preferred liquid film-forming carriers will comprise vinyl resins, such as polyvinyl alcohol, and polyvinyl pyrrilidone resins. Suitable polyvinyl alcohol resins are available from Monsanto, under the trade name Gelvatol and from DuPont under the trade name Elvanol. Suitable polyvinyl pyrrilidone polymers are available from GAF Chemicals under the trade names PVP K-25, PVP K-30, and PVP K-90. It will also be possible to employ commercially available nail polish formulations, as described in the Experimental section hereinafter.

Oxygen-scavenging substances suitable for incorporation into the compositions of the present invention will be able to prevent or reduce permeation of molecular oxygen through the film which is applied to the infected nail. The oxygen-scavenging substances must be biologically compatible, i.e., causing little or no immunological or other adverse reaction when topically present on the nail and in contact with the skin surrounding the nail. Moreover, the oxygen-scavenging substance must be chemically compatible with the liquid film-forming carrier and/or preformed film which is applied to the nail. The substances should further be stable, both in storage and after application to the nail, typically for at least several days after application, and preferably for at least one week or longer.

The concentration of the oxygen-scavenging substance in the liquid film-forming carrier and/or preformed film will be sufficient to inhibit oxygen penetration through the film so that growth of the aerobic fungi is inhibited or stopped. In particular, it is necessary that proliferation of the aerobic fungi be stopped so that the infection cannot increase or spread to other nails during the treatment period. It will be appreciated that potentially viable fungi may remain on or in the infected nail, particularly in the form of spores, which will not be killed by oxygen deprivation according to the present invention. Such spores and any other viable forms of the fungi, however, will be contained by the film during the treatment period and ultimately removed as the infected nail is replaced with new nail growth. Treatment according to the present invention will effectively prevent infection of the new nail growth with fungi or viable fungi spores.

The actual concentration of the oxygen-scavenging substance in the liquid carrier and oxygen barrier film will depend on the nature of the substance, the nature of the film, the thickness to which the film is applied, and a variety of other conditions which may vary with each particular application. Typically, the oxygen-scavenging substance will be present in the liquid film-forming composition at a weight percent of at least about 3% (dry weight basis), usually being at least about 10%, and preferably being at about 20% or greater.

Particular oxygen-scavenging substances which are useful in the compositions and methods of the present invention include transition metal chelates or complexes of salicylic acid or salt thereof, oxidizable organic acids or alcohols or derivatives thereof in combination with a catalyzing agent effective to enhance the oxygen-scavenging activity, and polycarboxylic acid chelates or complexes of a transition metal or a transition metal salt. Each of these classes of oxygen-scavenging substances will now be described in detail.

Suitable transition metal chelates and complexes of salicylic acid and salicylates, preferably in combination with reducing agents, are described in U.S. Pat. No. 5,364,555, the full disclosure of which is incorporated herein by reference. A preferred transitional metal chelate is an iron chelate of salicylic acid, in particular $Fe^{+++}/Sal_3$ where Sal=

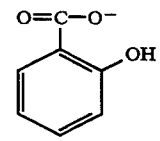

Instead of this material, a wide variety of other salicylates can be used, including

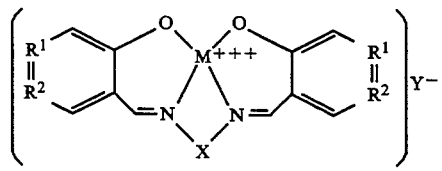

where M is a transition metal, X is $(CH_2)_m Z(CH_2)_n$ with m and n being integers and Z being N or C=C, with the proviso that if Z is N, then N is also bonded to M, and $R^1$ and $R^2$ being carbon atoms or part of a benzene ring, and Y is the counterion needed for charge neutrality.

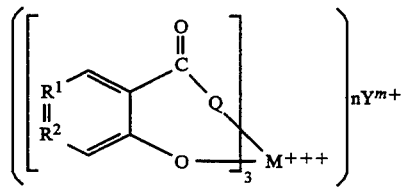

where M is a transition metal, Y is a counterion (typically an alkali metal), n and m are selected to provide charge neutrality, and $R^1$ and $R^2$ are carbon atoms or part of a benzene ring.

These salicylates are effective as oxygen scavengers because they react with oxygen to become oxidized. In addition, selection of a transition metal in its lower oxidation state enhances the oxygen scavenging performance of these chelates. As noted above, if transition metals in their higher oxidation state are utilized in these chelates, the oxygen scavenging properties of the chelate can be further enhanced by the incorporation of a reducing agent into the composition. Again, the ascorbates are preferred reducing agents. The ascorbates also act as a preservative for the chelate. In addition, the ascorbates can be included to augment the oxygen scavenging of the chelates.

The term "ascorbate compound" is used to include ascorbic acid in either its D or L form and any derivative, analog or salt thereof, including erythorbic acid. In particular, D- or L- ascorbic acid, and their sodium, potassium or calcium salts, or fatty acid derivatives may be used in this invention. Certain of the above, especially the sodium ascorbate salts, are particularly preferred because these materials have "Generally Recognized As Safe" (or "GRAS") status with the U.S. Food and Drug Administration.

Suitable oxidizable organic acids or alcohols are as follows. Preferred organic acids are ascorbate compounds, where the term "ascorbate compound" is used to include ascorbic acid in either its D or L form and any derivative, analog or salt thereof, including erythorbic acid. In particular, D- or L- ascorbic acid, their sodium, potassium or calcium salts, or fatty acid derivatives thereof may be used in this invention. The sodium salts are particularly preferred because these materials have "Generally Recognized As Safe" (or "GRAS") status with the U.S. Food and Drug Administration. It has been found that the ascorbate compound does not become active for scavenging oxygen until it contacts water or water vapor. Thus, the ascorbate compound is dispersed relatively uniformly throughout a polymer carrier which is permeable both to oxygen and water or water vapor. Thereafter, when the polymer is used in an application adjacent to or in the vicinity of a water bearing foodstuff, pharmaceutical, chemical, or beverage, water or water vapor will permeate into the polymer and thus activate the ascorbate compound for removal of oxygen. By retaining the polymer in a dry environment prior to use, the ascorbate compound will remain essentially dormant until activated.

The inclusion of a catalyzing agent in the organic acid and alcohol oxygen scavengers of the invention greatly enhances the rate of oxygen scavenging by the ascorbate compound after the ascorbate compound is activated by exposure to water or water vapor. It has been found that a transition metal compound, in the form of an organic or inorganic salt, or as a complex or chelate, is useful in accelerating (i.e., catalyzing) the rate of oxygen scavenging by the ascorbate compound. It is more preferred to use a simple iron or copper salt such as iron chloride or copper sulfate and to mix the same with the ascorbate compound for uniform dispersion throughout the polymer. Other suitable catalyzing agents include polyalkylamine chelates of a transition metal, macrocyclic amine chelates of a transition metal, and amino polycarboxylic acid chelates of a transition metal.

Other suitable organic acids and alcohols include gallic acid, pyrogallol, and propyl gallate.

Suitable polycarboxylic acid chelates or complexes of a transition metal or transition metal salt are described in U.S. Pat. No. 5,202,052, the full disclosure of which is incorporated herein by reference. A wide variety of polycarboxylic acid chelates or complexes of transition metals can be used in the formulations of this invention. Amino polycarboxylates, such as ethylenediamine tetraacetic acid (EDTA), and other polycarboxylates, optionally containing hydroxyl moieties, are representative examples of preferred compounds which can be complexed with the transition metal ion. Hydroxyethylene diamine triacetic acid, diethylene triamine pentaacetic acid, or trans-1,2-diamino cyclohexane tetraacetic acid can also be used as suitable amino polycarboxylic compounds. Other transition metal chelates containing one or more amine, hydroxyl, carboxylate or sulfhydryl groups, or combinations thereof, may also be used.

The most preferred oxygen scavenging materials include the iron complexes of ethylenediamine tetraacetic acid ("EDTA") or sodium salts thereof. $Fe^{+++}$/EDTA/($2Na+$) is the most preferred chelate. This material is dispersed relatively uniformly throughout the liquid film-forming carrier and/or film which is applied to the infected nail.

Although a particular advantage of the present invention is the ability to avoid the use of active anti-fungal drugs, in some cases it may be desirable to combine an anti-fungal drug in the compositions of the present invention in order to achieve an enhanced anti-fungal effect. Suitable anti-fungal drugs include polyene antibiotics, such as amphotericin B, amphotericin B methylester; mystatin; candicidin; griseofulvin; flucytosine; clotrimazoles, such as myconazole and ketoconazole; tolnaftate; and the like. Such anti-fungal drugs may be combined at concentrations known or expected to be therapeutically active or, in many cases, may be combined at concentrations below those needed to achieve therapeutic effectiveness in the absence of the oxygen-scavenging substances of the present invention.

Methods according to the present invention comprise depriving aerobic fungi present on or in an infected nail of oxygen availability by occluding the exposed surface of an infected nail for a time sufficient to inhibit growth of the fungi, preferably resulting in killing of the fungi. Usually, the nail surface will be occluded for a time sufficient to permit full replacement growth of a new nail. Thus, for fingernails, the treatment period will typically last at least 16 weeks, usually lasting at least 24 weeks, and frequently lasting 40 weeks or longer. For toenails, the treatment period will typically last at least 35 weeks, usually lasting at least 40 weeks, and frequently lasting 60 weeks, or longer.

In the case of a preformed oxygen barrier film, the film will typically be applied using a pressure sensitive adhesive on the film itself, or by using external bandages, adhesive strips, or the like. Such preformed oxygen barrier films can be replaced periodically according to a predetermined schedule or whenever they appear to be loosening or new nail growth has exposed potential new infection sites.

In the case of liquid film-forming compositions, the applied films will typically be removed and reapplied according to a predetermined schedule, typically at least weekly and usually not more often than daily.

The following examples are offered by way of illustration, not by way of limitation.

EXPERIMENTAL

Materials and Methods

Sodium ascorbate (2.6 gm) and ferric EDTA (5.4 gm) powders were combined in a clear nail polish base (Cutex brand, Strong Nail ® nail strengthener, product no. 1345, Chesebrough-Ponds, Inc.). The powders were passed through a #400 sieve to eliminate lumps and then thoroughly mixed into 15 ml volumes of the polish, until a total of 60 ml of polish had been added. After the final addition, the suspension was mixed with an electrically-driven mechanical stirrer. The suspension was returned to the original nail polish applicator bottles, with several 3 mm glass beads per bottle to provide stirring when the bottle is shaken.

The nail polish suspension prepared as above, was supplied to three patients suffering from onychomycosis. The suspension was applied by each patient as follows. The bottle was shaken before each application to resuspend the active ingredients. The entire surface of each fungus-infected nail was then covered with liquid polish and allowed to dry (2–3 minutes), and a second coat applied. This coating was removed weekly, with standard nail polish remover, and immediately reapplied. The coating was repaired at once if it cracked or flaked.

Results

Patient A: Female patient in mid-forties had onychomycosis of a fingernail. She was originally treated parenterally with ketoconazole (a systemic drug), but that treatment was discontinued due to side effects. After termination of the treatment, she experienced a severe recurrence of the infection. Four months after the discontinuance, she began treating using the above-described polish. After six weeks, she had a 2 mm wide clear (i.e., uninfected) zone of new nail at the base of the nail. The polish had arrested fungal growth, and the new growth (the clear zone) was uninfected. At week 12 of treatment, the clear zone was 4 mm wide, and the patient was continuing to use the treatment.

Patient B: Female patient in her early fifties had onychomycotic infection of five toenails on the same foot. After 6 weeks of polish therapy, the nails of the four small toes showed dramatic clearing. The nail on the great toe had been fully involved, and new nail appeared to be growing under the old (infected) nail plate. This could not be verified, however, without removal of the old nail, which was decided against by her dermatologist.

Patient C: Female patient in mid-thirties had had repetitive episodes of onychomycosis of the fingernails. She was treated parenterally with ketoconazole. During such treatment, clearing of the infection occurred, but the infection promptly recurred upon termination of the ketoconazole treatment. It would recur on one fingernail and promptly spread to other nails. Ketoconazole treatment was suspended, and the infection recurred as before. Thereafter, treatment with the above-described polish was commenced. When the polish treatment began, only one nail was infected. Only that infected nail was treated with the above-described polish. After four weeks of treatment, the infection has been arrested in that nail (as shown by a clear zone of new growth, uninfected nail). Furthermore, the infection had not spread to other nails, as it had done before. At ten weeks of treatment, the infected nail was virtually clear (100% uninfected), and no other nails had become infected. No side effects were noted by any patient, after prolonged use of the polish.

Although the foregoing invention has been described in detail for purposes of clarity of understanding, it will be obvious that certain modifications may be practiced within the scope of the appended claims.

What is claimed is:

1. A method for treating aerobic fungal infection of nails, said method comprising:
   forming a film over the nail, wherein the film comprises an amount of an oxygen-scavenging substance effective to substantially deprive aerobic fungi on or in the nail of oxygen, whereby fungal growth will be inhibited.
   said oxygen scavenging substances selected from the group consisting of a transition metal chelate or a complex of a salicylic acid or a salt thereof, an ascorbate compound and a polycarboxylic acid or aminopolycarboxylic acid chelate or complex of a transition metal or a salt thereof or a combination of a transition metal chelate or complex of a salicylic acid or a salt thereof and an ascorbate compound or a combination of a polycarboxylic acid or aminopolycarboxylic acid chelate or complex of a transition metal or a salt thereof and an ascorbate compound.

2. A method as in claim 1, wherein the film is formed by applying to the nail a liquid film-forming carrier comprising an oxygen-scavenging substance present in an amount sufficient to inhibit oxygen penetration through the resulting film.

3. A method as in claim 2, wherein the carrier is substantially free from active anti-fungal substances.

4. A method as in claim 2, wherein the carrier further comprises an active anti-fungal substance.

5. A method as in claim 2, wherein the film-forming carrier is a varnish comprising a resin in a solvent.

6. A method as in claim 5, wherein the resin is selected from the group consisting of cellulose resins, ethylene oxide resins, acrylic acid and acrylate resins, vinyl resins, and polyvinyl pyrrolidone resins.

7. A method for treating aerobic fungal infection of nails, said method comprising:
   forming a film over the nail, wherein the film comprises an amount of ascorbate compound and an amino polycarboxylate complex of a transition metal effective to substantially deprive aerobic fungi on or in the nail of oxygen, whereby fungal growth will be inhibited.

8. The method of claim 7 wherein the ascorbate compound is sodium ascorbate.

9. The method of claim 7 wherein amino polycarboxylate complex of a transition metal is ferric EDTA.

10. The method of claim 7 wherein the ascorbate compound is sodium ascorbate and the amino polycarboxylate complex of a transition metal is ferric EDTA.

* * * * *